United States Patent [19]
Kopf

[11] Patent Number: 6,048,727
[45] Date of Patent: Apr. 11, 2000

[54] APPARATUS AND METHOD FOR MASS TRANSFER INVOLVING BIOLOGICAL/ PHARMACEUTICAL MEDIA

[76] Inventor: Henry B. Kopf, 208 Coatbridge Cir., Cary, N.C. 27511

[21] Appl. No.: 07/442,240

[22] Filed: Nov. 28, 1989

Related U.S. Application Data

[62] Division of application No. 06/936,486, Nov. 26, 1986, Pat. No. 4,885,087.

[51] Int. Cl.$^7$ ...................................................... C12M 1/36
[52] U.S. Cl. .................. 435/383; 435/286.5; 435/297.4; 435/297.5; 435/299.1; 435/303.1; 435/308.1; 210/791
[58] Field of Search ...................................... 435/284–286, 435/813, 240, 242, 289, 313, 383, 286.5, 297.4, 297.5, 299.1, 303.1, 308.1; 210/601, 645, 793, 798, 791

[56] References Cited

U.S. PATENT DOCUMENTS

| | | | |
|---|---|---|---|
| 3,697,418 | 10/1972 | Johnson | 210/22 |
| 3,821,087 | 6/1974 | Knazek et al. | 195/127 |
| 3,883,393 | 5/1975 | Knazek et al. | 195/1.8 |
| 4,420,398 | 12/1983 | Castimo | 210/641 |
| 4,600,694 | 7/1986 | Clyde | 435/312 |
| 4,720,462 | 1/1988 | Rosenson | 435/285 |
| 4,724,548 | 2/1988 | Karrer | 435/240.1 |
| 4,885,087 | 12/1989 | Kopf | 210/321.72 |
| 4,889,812 | 12/1989 | Guinn et al. | 435/285 |

FOREIGN PATENT DOCUMENTS

| | | |
|---|---|---|
| 48-51905 | 3/1983 | Japan . |
| 61-88872 | 5/1986 | Japan . |
| 8401959 | 5/1984 | WIPO . |
| WO8602379 | 4/1986 | WIPO . |

OTHER PUBLICATIONS

"Continuous Hybridoma Growth and Monoclonal Antiboy Production in Hollow Fiber Reactors–Separators" Biotechnology an Bioengineering. May 28, 1986.

"CellTronics™ HF–100", Product Bulletin New Brunswick Scientific Company, Inc.

*Primary Examiner*—James C. Housel
*Attorney, Agent, or Firm*—Steven J. Hultquist

[57] ABSTRACT

A mass transfer apparatus and method is based upon use of a mass transfer chamber, such as a hollow fiber membrane bioreactor, with a control to change the directional flow therethrough for enhancement of the mass transfer operation. The invention has particular utility in cell growth systems, where the periodic reversal of flow direction of a nutrient stream passed through the bioreactor equalizes dispersion of cell growth through the bioreactor and enhances the transport of metabolic waste from the cells being grown.

13 Claims, 6 Drawing Sheets

APPARATUS AND METHOD FOR MASS TRANSFER INVOLVING BIOLOGICAL/ PHARMACEUTICAL MEDIA

CROSS-REFERENCE TO RELATED APPLICATION

This is a division of U.S. application Ser. No. 06/936,486 filed Nov. 26, 1986, and issued Dec. 5, 1989 as U.S. Pat. No. 4,885,087.

BACKGROUND OF THE INVENTION

1. Field of the Invention

This invention relates to apparatus and method for mass transfer involving biological/pharmaceutical media, as materials to or from which mass is being transferred.

2. Description of the Related Art

Mass transfer operations are used in numerous application areas for the concentration, purification, and separation of various biological/pharmaceutical media. Examples include: removal of sodium salts from pharmaceutical compositions to provide low-sodium products for human consumption; growth of cell cultures for research; removal of uric acid, creatinine, and various undesired electrolytes from blood, via hemodialysis; and the production and harvesting of viruses for vaccine production, or other intracellular products or secreted biologicals, such as immunoglobins, interleukens, interferons, clotting factors, and the like.

In applications of the above-described type, it is frequency practice to utilize a mass transfer chamber in which a mass transfer surface element is disposed which defines passages on its respective sides, in which the biological/ pharmaceutical medium is disposed on one side of the element, and the medium to which or from which mass transfer is to be effected, is disposed on the opposite side of the element. The respective media are contacted in their separate passages via the mass transfer element with one another, e.g., in countercurrent flow to one another, or with one of the materials retained in batch fashion in its passage (s) while the other material flows past the mass transfer element on its opposite side, to effect diffusional and/or osmolytic mass transfer.

A particular problem which has arisen in the operation of such systems is their tendency to experience fouling of the mass transfer element after a period of operation. As an illustration, in systems where cell media are grown by flow of a nutrient medium on one side of the mass transfer element, for diffusional transfer of nutrient species to a microbial culture on the opposite side of the element, the system after a period of operation experiences preferential areas of cell growth which inhibit further mass transfer. In other instances, where proteins are secreted by cellular media and subsequently transfused across the mass transfer element to a recipient medium, proteinaceous species deposit on the surfaces of the mass transfer element and create a physical barrier to continue diffusional transfer of the desired products.

These problems are particularly acute in mass transfer surface elements such as hollow fiber bundles, of the type wherein a plurality of interior passages accommodate flow of a first medium therethrough, while a second medium is contained in or flowed through the interstitial passages provided between adjacent hollow fibers in the bundle. Such hollow fiber mass transfer elements may have discrete fiber open area (inner diameter) dimensions on the order from about 0.25–1 mm, with pores in the mass transfer surface on the order of about 0.2 micron in diameter. Due to the small dimensions involved, these mass transfer elements are highly suspectible in operation to clogging and consequential reduction in the extent and rate of mass transfer.

In addition to hollow fiber membrane modules of the above-described type, sponge-like chambers or honeycomb-like modules are variously employed. The hollow fiber membrane modules, however, are currently the most widely employed in cell growth applications, blood dialysis, and various other application areas.

In the specific area of nutrient mass transfer cell growth systems, a severe problem in the use of the aforementioned mass transfer chambers is the formation of micro-environments within the chambers. Such micro-environments are characterized by poor growth rates, poor longevity of the microbial population, and most notably areas of active growth within the chamber compared to other areas therein apparently supporting little or no growth.

In these chambers, all cell types, both procaryotic and eucaryotic, when grown as suspension cultures or anchored to a perfusion matrix in the mass transfer chamber, have been observed to grow far more luxuriantly at one end of the chamber than the other. Neither agitation, as by the use of shaker apparatus, nor turning of the chamber to manually manipulate its orientation, has resolved the problem of formation of these inappropriate micro-environments.

It has been observed that the preferential growth areas are normally adjacent to the inlet flow of nutrient source to the mass transfer chamber, and that such active growth at the inlet terminal effectively causes the following problems: (1) poor utilization of total potential volume of the chamber for culturing; (2) poor diffusion of nutrient components within these regions of high cell growth; and (3) undesirable accumulation of metabolic wastes in and around the area of high cell growth, which may physically plague the desired nutrient mass transfer operation, particularly if such wastes deposit on the surfaces of the mass transfer element.

Accordingly, it is an object of the present invention to provide an improved apparatus and method for effecting mass transfer operations involving biological/ pharmaceutical media, in which the reduction of mass transfer attendant to prolonged operation is minimized.

It is another object of the invention to provide a system comprising a mass transfer chamber in which longitudinal decrease of mass transfer efficiency with prolonged operation, due to fouling of mass transfer surfaces, is minimized.

It is another object of the invention to provide improved apparatus and method for growing cells, in which undesireable formation of micro-environments, and areas of preferential growth, may be substantially avoided.

Other objects and advantages of the invention will be more fully apparent from the ensuing disclosure and appended claims.

SUMMARY OF THE INVENTION

In a broad apparatus aspect, the invention relates to a mass transfer apparatus comprising:

(a) a pump having discharge and inlet ports;
(b) an elongated mass transfer chamber having first and second inlets at opposite ends thereof;
(c) a reservoir having inlet and outlet ports;
(d) switchable flow control means comprising flow ports designated A, B, C, and D, for connecting:
(1) in a first configuration, port A in flow communication with port B, and port C in flow communication with step D; and (2) in a second configuration, port A in flow communication with port D, and port B in flow communication with port C;

(e) conduits connecting the pump discharge port to port C, the pump inlet to the reservoir outlet port, the reservoir inlet port to port A, the chamber first inlet to port B, and the chamber second inlet to port D.

The switchable flow control means of the above-described apparatus may be any suitable means providing flow communication in the aforementioned manner between the respective conduits in paragraph (e), e.g., a four-way valve, or a series of valves and/or reservoirs, etc., and accordingly the term "port" is to be broadly construed to include any suitable means of coupling the various conduits so that such switching of flow may be effected. A preferred switchable flow control means is a four-way valve having four ports for coupling of the respective conduits.

In another aspect, the apparatus as broadly described above comprises at least one mass transfer surface element in the chamber defining passages on its respective sides, with passage(s) on one side of the mass transfer element(s) communicating with the first and second inlets for flow of a first medium therethrough in mass exchange relationship with a second medium in the passage(s) on the other side of the mass transfer element(s).

Such apparatus may further comprise:

(i) a port on the mass transfer chamber communicating with the aforementioned second medium passage(s); and (ii) two serially-connected valves at the port in flow communication with the second medium passage(s), comprising a first valve contiguous to the port and a second valve connected to the first valve in series therewith, whereby second medium may be introduced to and withdrawn from the mass exchange chamber by flow through the port and its associated serially-connected valves, and the first valve may be closed to retain second medium in the mass exchange chamber while the second valve is open to permit its sterilization.

A further aspect of the apparatus described above comprises: (1) ports on the mass exchange chamber communicating with the second medium passage(s); (2) conduits joining the ports on the mass exchange chamber to form a second medium flow circuit with which is coupled (3) a second pump to circulate the second medium therethrough; and (4) means for intermittently actuating the pump in accordance with a predetermined periodic cycle.

In a further aspect, the above-described apparatus comprises:

variable-speed agitation means for agitating contents of the reservoir; and control means for the apparatus, comprising:

(I) means for remotely and alternately positioning the switchable flow control means;

(II) means for remotely varying the speed of the agitation means;

(III) means for remotely varying the pumping rate of the pump connected to the reservoir outlet port; and (IV) means for remotely varying the pumping rate of the second pump when actuated by the intermittent actuating means.

A preferred form of such apparatus comprises as a centralized module a unitary structural housing containing such remote control means (I), (II), (III), and (IV), and the intermittent actuating means.

In a method aspect, the invention relates to a mass transfer method comprising:

(a) establishing a mass transfer system which includes:

(i) a pump having inlet and discharge ports;

(ii) an elongated mass transfer chamber having first and second inlets at opposite ends of the chamber to accommodate flow of a first mass transfer medium therethrough in mass transfer relationship with a second mass transfer medium therein;

(iii) a first mass transfer medium reservoir having inlet and outlet ports;

(iv) switchable flow control means comprising flow ports designated A, B, C, and D, for connecting:

(1) in a first configuration, port A in flow communication with port B, and port C in flow communication with step D; and (2) in a second configuration, port A in flow communication with port D, and port B in flow communication with port C;

(v) conduits connecting the pump discharge port to port C, the pump inlet port to the reservoir outlet port, the reservoir inlet port to port A, the chamber first inlet to port B, and the chamber second inlet to the valve port D;

(b) operating the pump to establish flow of the first medium through the mass transfer chamber in a selected direction; and (c) periodically repositioning the switchable flow control means so as to sequentially change according to a predetermined schedule the direction of flow of the first medium through the mass transfer chamber.

The second medium by way of illustration may be selected from the group consisting of cell cultures, blood, and pharmaceutical compositions.

Other method aspects of the invention include those corresponding to the operation of the various apparatus aspects of the invention described above. A specifically preferred method aspect of the invention relates to a cell growth method comprising:

(a) establishing a sterile growth system which includes:

(i) a pump having inlet and outlet ports;

(ii) an elongated cell growth chamber having first and second inlets at opposite ends of the chamber;

(iii) reservoir having inlet and outlet ports;

(iv) switchable flow control means comprising flow ports designated A, B, C, and D, for connecting:

(1) in a first configuration, port A in flow communication with port B, and port C in flow communication with step D; and (2) in a second configuration, port A in flow communication with port D, and port B in flow communication with port C;

(v) conduit connecting the pump discharge port to port C, the pump inlet port to the reservoir outlet port, the reservoir inlet port to port A, the chamber first inlet to port B, and the chamber second inlet to port D;

(b) introducing culture medium to the system;

(c) inoculating the chamber with a selected cell type;

(d) operating the pump to establish flow of the medium through the growth chamber in a selected direction;

(e) incubating the system for a selected period and during such period changing the medium if and as required for the selected medium; and (f) periodically repositioning the switchable flow control means so as to sequentially change according to a predetermined schedule the direction of flow of the medium through the growth chamber, to substantially uniformly disperse cell growth throughout the chamber and transport metabolic waste away from the cells being grown in the chamber.

Other aspects and features of the invention will be more fully apparent from the description set forth hereinafter.

DETAILED DESCRIPTION OF THE INVENTION AND PREFERRED EMBODIMENTS THEREOF

Having repeatedly observed that cell growth in cellular and nutrient media mass transfer systems is in direct relationship to the inlet of fresh nutrient media, it was hypothesized that altering the direction of flow of the nutrient source to the chamber would result in greater uniformity of growth within the chamber. Additional factors observed were that the increased agitation from such a flow scheme would enhance back transport of metabolic waste as well as increase the homogeneity with respect to pH and gas exchange in the cellular medium. A successful apparatus and method is based on the use of a switchable flow control means, preferably a four-way valve which enables the direction of fluid flow to be reversed by activation of one valve alone.

Figure 1:
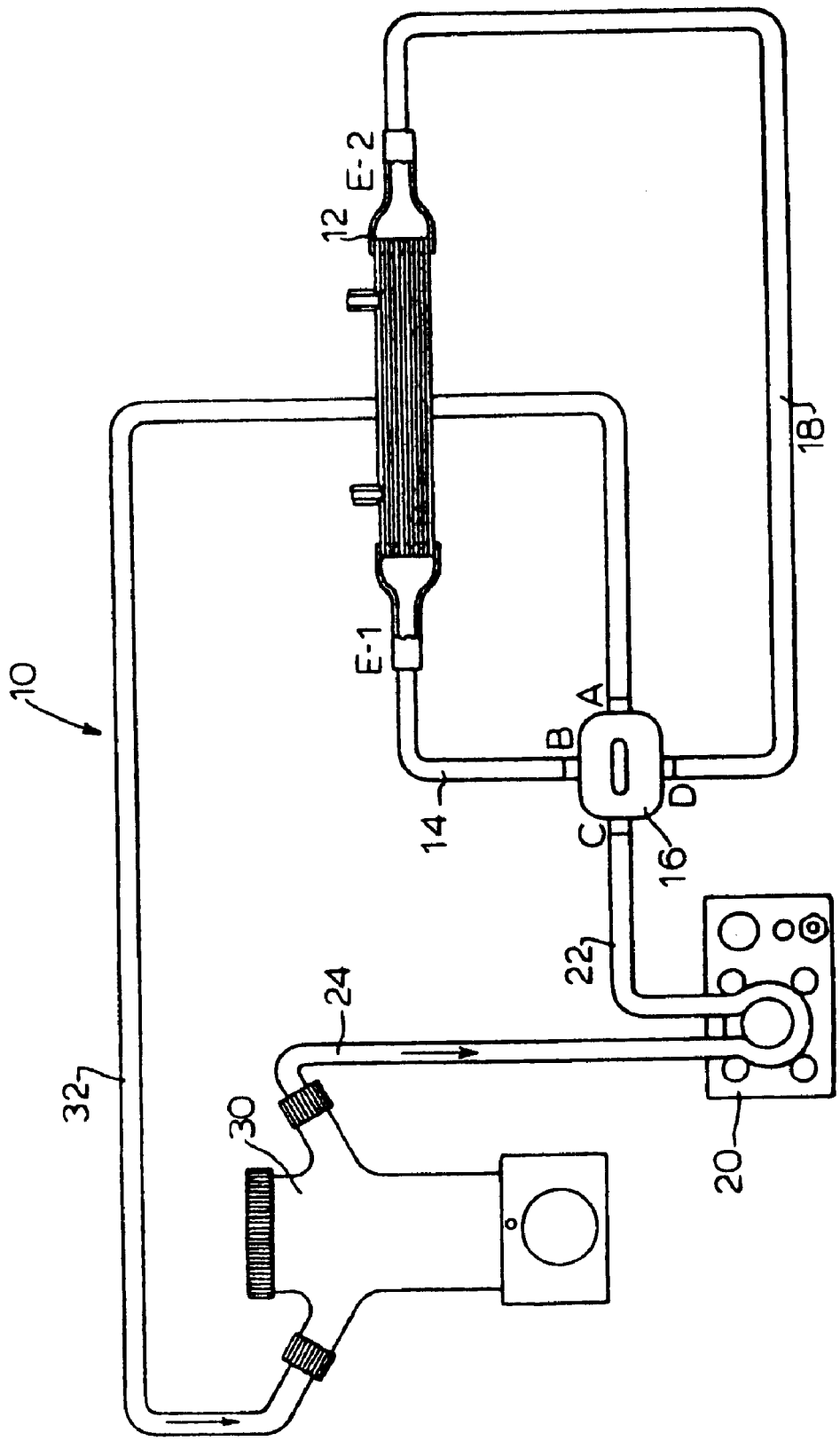
FIG. 1 is a schematic diagram of a cell culture system incorporating a four-way valve in accordance with the invention.

Referring now to the drawings, FIG. 1 shows an illustrative nutrient delivery cell growth system 10 utilizing a hollow fiber membrane 12 of conventional type as the bioreactor. The bioreactor comprised a bundle of hollow fibers, e.g., of from 1 to about 3 inches in diameter, presenting on the order of 60% open area in cross-section. The internal diameter of individual fibers in the bundle may for example be from about 0.25 to about 1 mm, with pores for diffusional and/or osmolytic transfer of nutrient species, in the wall of the tubular fibers, of about 0.2 micron diameter.

Illustrative hollow fiber membrane mass transfer elements suited to the practice of the invention are made by A/G Technologies, Needam, Mass., and Cordis Corporation, Miami, Fla.

The hollow fiber membrane 12 is connected at one end, designated E-1, by conduit 14 to a port designated D, which is one of four such ports, the others being designated A, B, and C, of a four way valve 16. The conduit may be a flexible, elastic silicone tubing, or may be formed of a more rigid material such as 316 stainless steel tubing. The opposite end of the hollow fiber membrane 12, designated E-2, is connected by conduit 18 to port B of the 4-way valve 16. A 4-way LL valve 16 generally useful in the broad practice of the invention is manufactured by Quality Controls Company, Tilton, N.H.

The bioreactor system shown in FIG. 1 also includes a variable speed pump 20, which may for example comprise the peristaltic pump 20 illustrated in FIG. 1, such as is commercially available from Cole-Palmer Company, Chicago, Ill., or a variable speed gear pump, such as the MICROPUMP® gear pump, commercially available from MICROPUMP Corporation, Concord, Calif.

Pump 20 is connected on its discharge side by conduit 22 to port C of the 4-way valve 16. The inlet side of pump 20 is connected by conduit 24 to the outlet port of a reservoir 30 containing the nutrient medium for the bioreactor system. Such reservoir may be of a type commercially available from Bellco Company, Vineland, N.J. The inlet end of the reservoir 30 is connected through another conduit 32 to port A of the 4-way valve 16.

The reservoir 30 is disposed on a magnetic stirrer device 35 which provides agitation of the contents of the reservoir. The magnetic stirrer may suitably be of a type having a variable speed, to provide a varying level of agitation in the reservoir 30 depending on the density and suspension characteristics of the nutrient medium contained therein.

The mass transfer chamber comprising the hollow fiber membrane 12 also features a first port 38 in proximity to inlet E-1, and a second port 40 proximate to inlet E-2. These ports may be provided with suitable closure means, or may be joined with suitable flow circuitry, as hereinafter described in greater detail, for circulation of the cellular medium contained in the hollow fiber membrane 12.

Thus, in this embodiment, the cellular medium is disposed in one set of passages in membrane 12, which are defined by the interstitial spaces between neighboring hollow fibers in the bundle. Such bundles are typically potted at their ends in urethane or epoxy resins, so that they may be suitably headered to accomodate flow through the interior passages of the hollow fibers, without leakage into the interstitial passages. The nutrient thus is flowed longitudinally through the interior passages of the hollow fibers, and nutrient species transfuse through the fiber walls to the cellular culture contained in the interstitial passages of the bundle.

4-way valve 16 has two positions. In what will be referred to as a first position, port C is connected to port D and port B is connected to port A. In this mode, the nutrient broth in conduit 24 from reservoir 30 is flowed by pump 20 into conduit 22, from which it enters port C, discharges through port D into conduit 18 and enters the hollow fiber membrane bioreactor at its inlet designated E-2. At the same time the contacted nutrient broth exits through the opposite end, designated as inlet E-2, of the mass transfer chamber and passes through ports B and A of 4-way valve 16 to be returned through conduit 32 to the inlet of reservoir 30, from which the nutrient medium is circulated in the previously described manner.

When the 4-way valve 16 is in what will be referred to as its second position, port C is connected to port B and thus the valve discharges the nutrient broth into conduit 14 from which it enters the mass transfer chamber containing the hollow fiber membrane, at the inlet designated E-1, passes through the interior passages of the hollow fibers and exits at the opposite end of the mass transfer chamber, designated E-2, for return in conduit 18 through ports D and A of 4-way valve 16 and conduit 32 to the reservoir 30.

Figure 2:
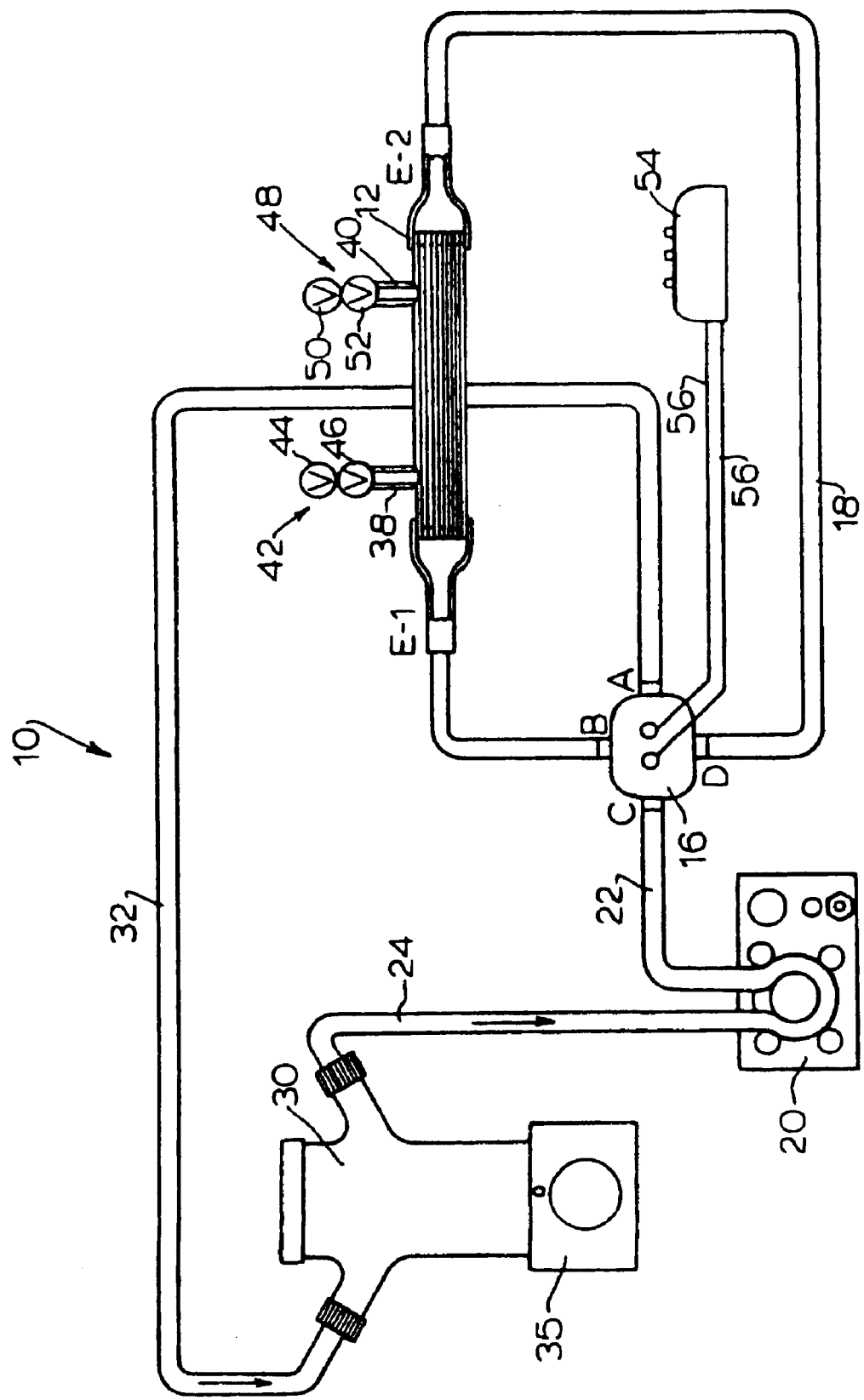
FIG. 2 is a schematic diagram of the cell culture system of FIG. 1 with a remote control arrangement for the four-way valve.

Switching of the 4-way valve may be accomplished either manually or through an automatic actuator such as is schematically illustrated in FIG. 2, in which the valve 16 is controlled by a suitable automatic controller 54, operatively connected to the valve assembly by control signal wires 56. The continued operation of the bioreactor system with repositioning of the valve 16 either manually or by remote control, of e.g., a pneumatic or electrical actuator, thus results in a balanced delivery of nutrients to the mass transfer chamber alternately from its respective ends. Periodic switching of flow in this manner, in accordance with a predetermined cyclic schedule, also enhances the transport of metabolic wastes away from the cells. Further, the increased agitation incident to the switching of nutrient flows results in a more homogeneous environment with respect to other metabolic parameters.

Apart from the cyclic 4-way valve switching means previously described, the FIG. 2 system is identical in all respects with that of FIG. 1, except for the provision at each of the ports 38 and 40, of two valves in series. At the first port 38, the valve assembly 42 comprises a first valve 46 contiguous to the port, and a second valve 44 connected in series with the first valve, as shown. A similar construction is employed at second port 40, where the double valve assembly 48 comprises a first valve 52 and a second outer valve 50.

The double valve arrangement described in the preceding paragraph is highly preferred in practice, since it permits cellular inoculation of the interstitial passages in the hollow fiber bundle, as well as withdrawal of the product cell culture from the interstitial passages, in a manner enabling complete sterility of the apparatus to be maintained. Specifically, in the prior practice of utilizing ported hollow fiber cell growth chambers, only one valve has been employed on each port. In such single valve assembly, the introduction to or withdrawal from the mass transfer chamber of the cellular medium results in sterility of the valve's interior surfaces being lost, raising the potential for contamination of the mass transfer chamber, unless the apparatus is thereupon fully shut down, and the valves removed and autoclaved. Although some attempts have been made in the past to sterilize single-valved ports by directing superheated steam against the valve body structure, such mode of sterilization does not reach the interior surfaces of the valve, which must be closed to retain the contents in the mass transfer chamber.

By contrast, the double valve arrangement shown permits ready sterilization of the valve assembly in a manner which perserves the sterility of the associated apparatus, by the simple expedient of opening the outermost valve (42, or 48) while the corresponding inner valve (46, or 52) is kept closed, and superheated steam, or other sterilant, is directed into the opened outer valve, to effect complete sterilization thereof. In this manner, a sterile barrier is maintained at the mass transfer chamber even during continuous operation, and without the necessity of shutting down the apparatus for autoclaving of the valve elements. Although simple in character, this double-valved construction is a significant advance in the art, due to the criticality of sterility in cell growth as well as in numerous other mass transfer operations in which bioreactors of the type shown in FIGS. 1 and 2 may be employed.

Figure 3:
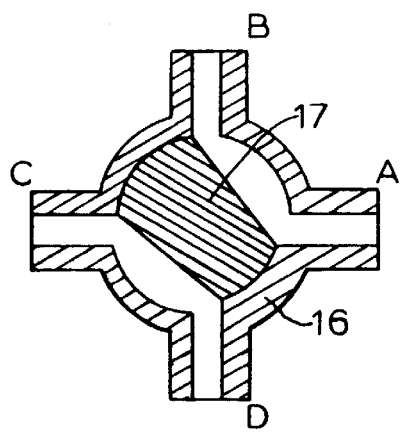
FIG. 3 is a schematic diagram of the four-way valve in a first position.
Figure 4:
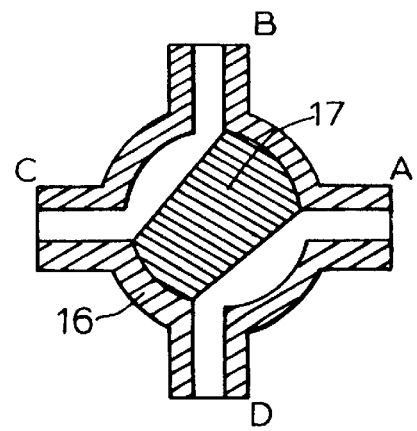
FIG. 4 is a schematic diagram of the four-way valve in a second position.

FIGS. 3 and 4 are simplified schematic illustrations of the interior flow passages of an illustrative 4-way valve of the general type previously described in connection with FIGS. 1 and 2. FIG. 3 shows the 4-way valve in a first position, in which the interior element 17 of the valve 16 is oriented so that valve ports B and A are in flow communication with one another, and ports C and D are in flow communication with each other. By a 90° rotation of the valve element 17, the configuration shown in FIG. 4, designated as the second position, is achieved. In this position, valve ports B and C are in fluid communication with one another, while flow communication is likewise established between ports A and D. By reference again to the systems schematically illustrated in FIGS. 1 and 2, it can be seen that the alternation of the valve position, between the respective configurations shown in FIGS. 3 and 4, will effect a cyclic alternating switching of the nutrient medium flow to the respective ends of the mass transfer chamber containing hollow fiber membrane 12.

Although the mass transfer chamber has been described with specific reference to a hollow fiber bundle as the mass transfer surface element, it is within the purview of the invention to utilize other mass transfer elements, such as planer membranes, through which mass transfer may be effected, it being further understood that the number of specific passges within the mass transfer chamber may be varied widely depending on the specific mass transfer media and application employed.

Figure 5:
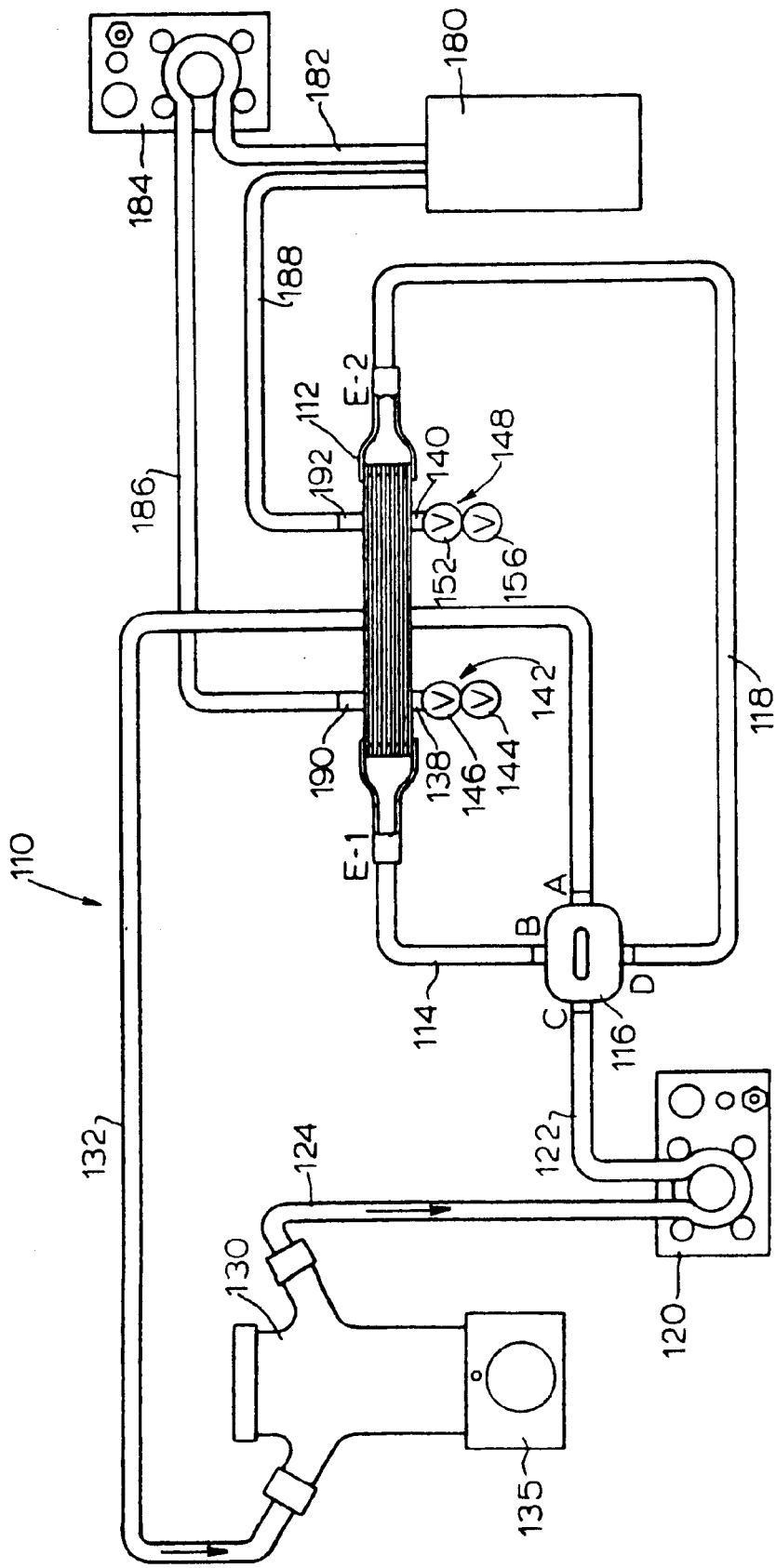
FIG. 5 is a schematic diagram of a mass transfer system which may be usefully employed in dialysis-type extractions of blood components or for de-salting of pharmaceutical compositions.

FIG. 5 is a schematic diagram of mass transfer system which may be employed for mass transfer operations other than the cell growth processes illustratively described in connection with the FIGS. 1 and 2 embodiments. The FIG. 5 apparatus may, for example, have utility for mass transfer operations such as: desalting of pharmaceutical compositions; desalting, extraction, or fractionation of blood, plasma, or serum materials; and harvesting of secreted or intracellularly produced biological materials, such as interferons, interleukins, immunoglobins, growth factors, clotting factors, etc.

In FIG. 5, all system elements corresponding to those shown in FIG. 1 and 2 are numbered correspondingly therewith, by addition of 100 to the corresponding reference numbers of FIG. 1–2.

In this mass transfer system, the mass transfer chamber contains a hollow fiber bundle 112 which provides a first set of interior passages in the constituent hollow fibers through which a first medium, supplied from reservoir 130, is flowed. Concurrently, a second mass transfer medium, stored in second reservoir 180, is withdrawn in conduit 182, passed to peristaltic pump 184, and discharged into conduit 186 from which it enters the mass transfer chamber at port 190 and longitudinally flows through the interstitial passages in the hollow fiber bundle. After such longitudinal flow, in which the second medium is contacted with the first mass transfer medium concurrently flowed through the interior passages of the hollow fiber bundle, the contacted second medium is discharged from the mass transfer chamber in port 192 and flowed in conduit 188 back to second reservoir 180. A sterile barrier at the mass transfer chamber may be provided by double valve assemblies 142 and 148, as shown on the third and fourth ports, 138 and 140, respectively, of the mass transfer chamber.

Figure 6:
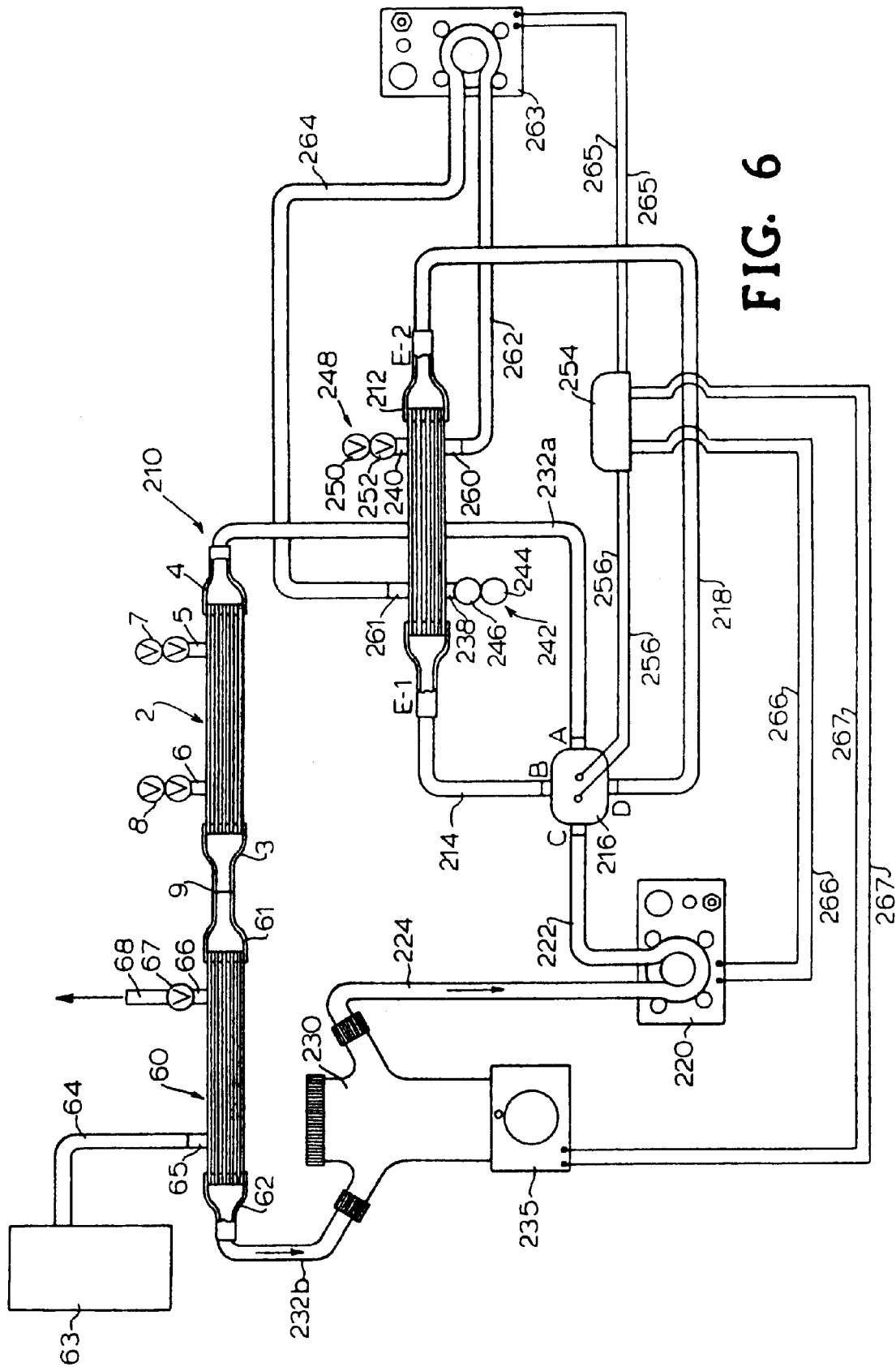
FIG. 6 is a schematic diagram of a cell growth system of a general type as shown in FIG. 2, but modified by the further addition of sterile barrier means for introducing or buffering nutrient solution and for oxygenating the nutrient solution on its return to the reservoir, and in which a unitary remote control means is employed.

FIG. 6 shows a modification of the cellular growth system shown in FIG. 2, wherein corresponding system elements have been numbered correspondingly with reference to FIG. 2, by addition of 200 to the reference numerals of the same or corresponding FIG. 2 elements.

As in the FIG. 2 embodiment, the mass transfer chamber comprises a hollow fiber bundle 212 whose interior flow passages, inside the hollow fibers, communicate with respective inlets E-1 and E-2 of the chamber, which in turn are joined respectively by conduits 214 and 218 to ports B and D of the valve assembly 216. Port C of the valve assembly is coupled with conduit 22, and port A with conduit 232a, to provide for reversing flow through the mass transfer chamber upon switching of the valve assembly in the aforedescribed manner. The valve assembly comprises a actuator which is actuated by control signals transmitted in a signal wires 256 from the unitary remote control 254, as described in greater detail hereinafter.

As in the FIG. 2 system, the system shown in FIG. 6 has first and second ports 238 and 240 on the mass transfer chamber, to which are connected dual valve assemblies 242 and 248, respectively. The mass transfer chamber further includes a third port 260 and a fourth port 261, which are joined to an external flow circuit comprising conduits 262 and 264, respectively, whereby the cellular culture or other second medium may be withdrawn from the interstitial passages of the hollow fiber bundle 212 and circulated through the external flow circuit by means of the pump 263 coupled therewith.

The remote control unit 254 is joined in controlling relationship with the peristaltic pump 263 by means of control signal transmission wires 265, so that the pump 263 is periodically actuated and operated for a predetermined time to circulate the cellular mass externally of the mass transfer chamber. This effects redistribution and agitation of the cellular mass, and significantly enhances mass transfer efficiency of the system, resulting in a more uniform distribution of cellular growth in the hollow fiber bioreactor. By way of example, in some cellular systems it has been found to be advantageous to operate the pump 263 on a six minute cycle time program, comprising active pumping for periods on the order of about one minute in duration, and quiescent intervals between active pumping, during which the pump 263 is deactivated, of approximately five minutes.

The remote control unit 254 is also operatively coupled with peristaltic pump 220, via control signal transmission wires 266, and with magnetic stirrer 235, via control signal transmission wires 267.

By such arrangement, peristaltic pumps 220 and 263, 4-way valve assembly 216, and magnetic stirrer 235, can all be controlled from a single remote locus, thereby simplifying the construction and operation of the system, relative to the use of multiple remote control means.

As in the FIG. 2 system, nutrient broth is retained in reservoir 230, from which it is circulated in conduit 224 by pump 220 into conduit 222 for passage to inlet end E-1 or E-2 of the mass transfer chamber, depending on the position of the 4-way valve assembly 216.

Depending on this valve position, the effluent nutrient broth is discharged from the mass transfer chamber in either conduit 214 or 218 and passed via the return flow conduit 232, comprising conduit segments 232a and 232b, to the reservoir 230.

In this return flow conduit 232 comprising the conduit segments 232a and 232b, is disposed a second hollow fiber mass transfer chamber 2 having an inlet end 4 and an outlet end 3, constructed analogously to the previously described mass transfer chamber comprising hollow fiber membrane 212. The second mass transfer chamber is provided with a first port 5 coupled with a double valve assembly 7, and a second port 6, having connected thereto the double valve assembly 8.

At its outlet end 3, the second mass transfer chamber is coupled to the inlet 61 of a third mass transfer chamber 60 comprising a hollow fiber mass transfer element, by suitable coupling means 9 of a conventional type known in the art. The outlet end 62 of the third mass transfer chamber in turn is coupled to the aforementioned conduit segment 232b.

The third mass transfer chamber 60 has a first port 65, to which is joined an oxygen gas supply means 63, via the connecting conduit 64. By such arrangement, oxygen from the supply means is passed to the interstitial passages of the hollow fiber bundle of the third mass transfer chamber 60. This chamber has a second port 66 provided with a flow control valve 67 connected to a discharge conduit 68, for controllable egress of contacted gas therefrom.

In operation, the nutrient broth contacted with the cellular culture in the mass transfer chamber comprising hollow fiber membrane 212, prior to being returned to the reservoir 230, passes in conduit 232a to the second mass transfer chamber 2, whose doubly-valved ports provide a sterile barrier to exterior contamination of the system. By such expedient, the reservoir 230 may be retained in completely closed condition during the operation of the system, and additional nutrient materials and/or additives to the nutrient broth, may be introduced to the sytem through ports 5 and/or 6, for flow into the interstitial passages of the second mass transfer chamber, and diffusional and/or osmolytic transfer into the nutrient broth being returned to the reservoir in the interior passages of the hollow fiber bundle. Thus, the returned nutrient broth may be buffered, purified, etc., by means of the second mass transfer chamber, without breaching of the sterile barrier provided thereby. After introduction or removal of medium through the ports 5 or 6, the port may be sterilized by opening of the outer valve of the double valve assembly, while the inner valve is retained in closed position, and introducing a sterilant onto the interior and exterior surfaces of the outer valve, in the previously described manner.

For growth of aerobic cellular cultures in the first mass transfer chamber comprising the hollow fiber bundle 212, it is important to maintain a suitable disolved oxygen content in the nutrient broth being supplied by the reservoir 230. Oxygenation of the nutrient medium is effected in the FIG. 6 system by the third mass transfer chamber 60. Oxygen gas from source 63 is introduced in conduit 64 and enters the third mass transfer chamber in port 65, from which it enters the interstitial passages in the hollow fiber bundle and perfuses into the interior passages of the hollow fiber bundle containing the flowing nutrient medium. Oxygen-depleted gas from the mass transfer contacting operation is discharged from the third chamber by port 66 and flows into discharge conduit 68, as controlled by flow control valve 67. The flow control valve 67 may be feedback-controlled by suitable coupling with an oxygen sensing means, such as a dissolved oxygen probe in the nutrient broth in reservoir 230, or an oxygen-sensing gas analyzer which is employed to sense the oxygen content of the vent gas from conduit 68, whereby the flow control valve 67 may be adjusted responsively to the oxygen concentration sensing, so that the oxygen content of the nutrient broth in reservoir 230 is maintained at a predetermined level.

Figure 7:
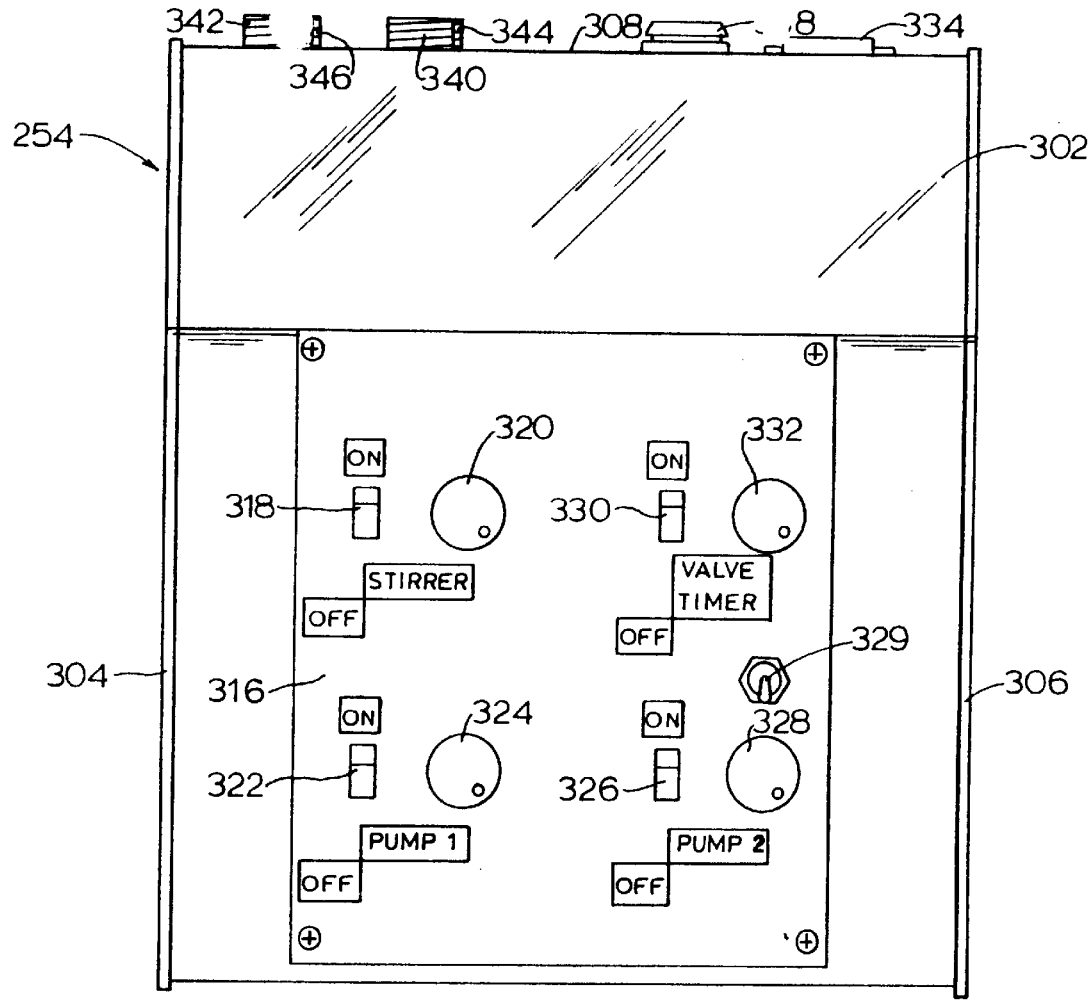
FIG. 7 is a plan view of a unitary remote control apparatus such as may be usefully employed in systems of the type shown in FIG. 6.
Figure 8:
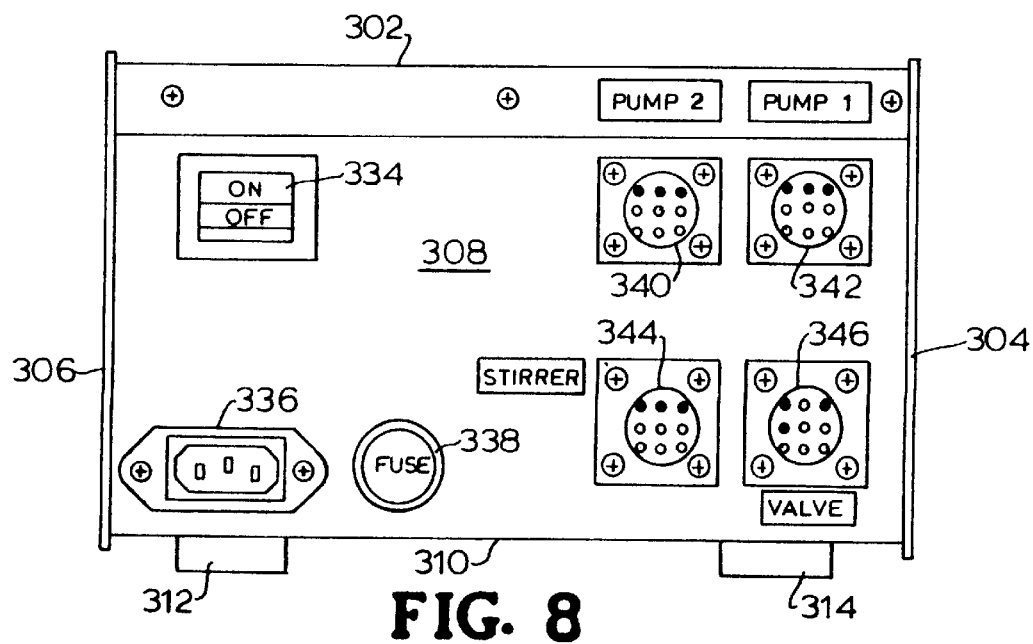
FIG. 8 is a rear elevational view of the FIG. 7 apparatus.

FIGS. 7 and 8 show the structural features of the unitary remote control unit 254 schematically illustrated in FIG. 6. In this remote control unit, the electronic control circuitry is contained in a housing comprising a top member 302, bottom member 310, sidewalls 304 and 306, and a rear wall 308.

On the top member 302 is disposed a control panel 316 comprising an on-off switch 318 for the magnetic stirrer control 320, which may be manually adjusted to establish a predetermined rotational speed for the magnetic stirrer 235 (see FIG. 6).

On-off switch 330 energizes the valve timer control 332, which may be manually adjusted to vary the switching frequency of the 4-way valve assembly 216 of FIG. 6. In practice, it has been found advantageous to construct the valve timer control to provide switching intervals over a range of one minute increments, from one to five minutes, so that flow of nutrients through the cell growth mass transfer chamber may be periodically reversed at and of such predetermined time intervals, in accordance with a selected schedule of operation for the given system.

On-off switch 322 energizes the pump control 324, which is manually adjustable to establish a predetermined rotational speed for pump 220 in FIG. 6.

In like manner, on=off switch 326 energizes the pump control 328, which is manually adjustable to provide a predetermined rotational speed for the pump 263.

FIG. 8 shows the details of the back wall 308 of the remote control unit. The remote control unit as shown is supported on casters 312 and 314, which may be of a resilient material such as neoprene rubber to dampen the vibrations of the system and prevent damage to the electronic circuitry contained within the unit.

Electrical power is supplied to the electronic circuitry in the unit by means of power cord coupling socket 336, adjacent to which is a fuse holder 338 containing a suitably sized fuse for protection of the electronic circuitry. Master switch 334 provides for electrical energizing of the circuitry in the unit.

At the right hand side of back wall 308, as shown in FIG. 8, are provided suitable electrical sockets, for coupling of the remote control unit to the control signal transmitting wires for the controlled elements of the system. Thus, socket 340 accommodates a plug connected to signal control wires 365, socket 342 accommodates a plug coupled to signal control wires 266, socket 344 accommodates a plug coupled to signal control wires 267, and socket 346 accommodates a plug coupled to signal control wires 256, with reference to the control wires as identified in FIG. 6.

Figure 9:
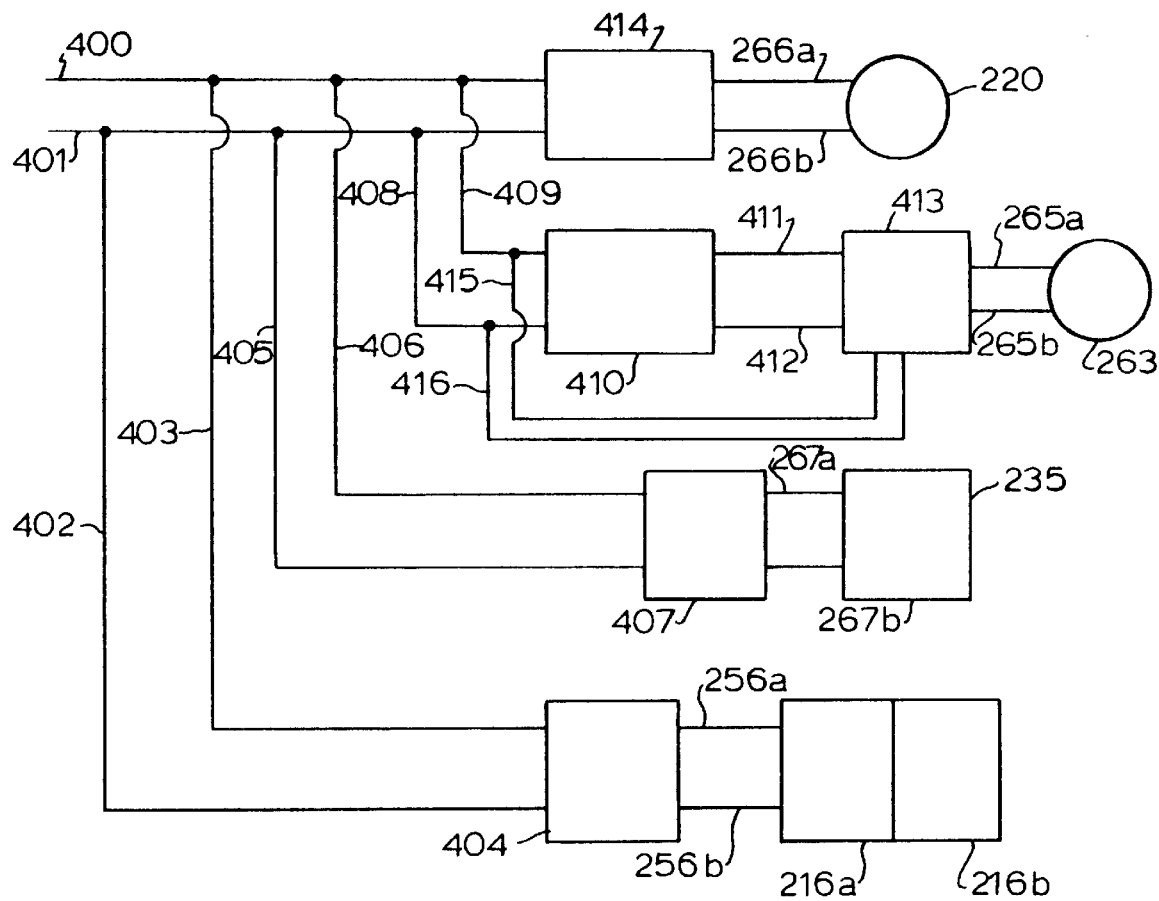
FIG. 9 is a schematic representation of elements of the remote control system and the system components controlled thereby.

FIG. 9 is a schematic electrical diagram of the remote control system and associated controlled elements.

Power to the remote control unit is introduced in power lines 400 and 401 (as connected to the remote control unit by an associated plug at socket 336, as shown in FIG. 8).

Power from the main power lines is transmitted to variable speed control 414 from which electrical control signals are passed in wires 266a and 266b to pump 220.

Branch power lines 408 and 409 convey power to the timing device 410 coupled by control signal wires 411 and 412 to the variable speed control 413, in turn coupled in signal controlling relationship with pump 263 by means of signal wires 265a and 265b. Branch lines 415 and 416 pass electrical power from lines 408 and 409, respectively, directly to the variable speed control 413. In such manner, the variable speed control is energized during the period that the timing device determines for active operation of pump 263, consistent with the aforedescribed use of pump 263 to periodically circulate nutrient broth in the external flow circuit comprising conduits 262 and 264 (see FIG. 6). During the intervening periods of quiescence, in which the external flow circuit is not employed, the timing device 410 receives power from branch lines 408 and 409, but does not operate to actuate the variable speed control.

Branch power lines 405 and 406 convey power to speed control 407 which is coupled by signal control transmission wires 267a and 267b to magnetic stirrer 235, whereby a predetermined rotational speed of the magnetic stirrer may be effected.

Finally, branch power lines 402 and 403 convey power to the timing device 404 which is coupled in signal controlling relationship with the 4-way valve assembly comprising valve actuator 216a and valve 216b, by means of the signal transmission wires 256a and 256b.

The specific construction and arrangement of the electronic circuitry for the variable speed controls and timing devices may be conventional in character, and may vary widely in specific features, it being required only that such circuitry is suitably consolidated when utilized in a unitary remote control, as illustratively shown in FIGS. 7 and 8.

The features and advantages of the invention are more fully shown with reference to the following examples, wherein all parts and percentages are by weight, unless otherwise expressly stated.

EXAMPLE I

A hollow fiber bioreactor system 10 was constructed as previously described in FIG. 1. This system was chemically sterilized using hypochlorite solution and flushed with sterile deionized water. The system was then filled with culture medium, RPMI 1640 with 5% fetal calf serum, and incubated for 48 hours at 37° C. in a 5% carbon dioxide, no humidity environment, as a check for sterility and system equilibration.

An inoculum of cell type EL-4-IL-2 was prepared from stock cultures and inoculated into the extracapillary space of the hollow fiber bioreactor. The system was again incubated for 20 days with media being changed as required in accordance with prior practice for this cell type. The four way LL valve 16 was switched each half hour during the working day and once each night, usually about midnight, taking care to use alternate positioning on successive nights.

The specific cell culture utilized was previously grown in membrane bioreactors and observed to grow denser at the inlet end. In this experiment, with the four way LL valve 16, the cell growth was equally dispersed throughout the growth chamber 12. The cell type utilized is commonly referred to as a suspension culture which allows for ease of visualization of cell growth by simple liquid turbidity observation.

EXAMPLE II

A simple hollow fiber bioreactor system 10 was constructed as previously described in FIG. 1. This system was then filled with culture medium, MEM with Earles Salts, non-essential amino acids, and 10% fetal calf serum, and incubated for 48 hours at 37° C. in a 5% carbon dioxide, no humidity environment, as a check for sterility and system equilibration.

An inoculum of cell type BALB-3T3 was prepared from stock cultures and inoculated into the extracapillary space of the hollow fiber bioreactor. The system was then incubated for an additional 30 days, changing media as required in accordance with prior practice for this cell type. The four way LL valve 16 was switched each half hour during the working day and once each night, usually about midnight, taking care to use alternate positioning on successive nights.

the culture utilized in this example was previously grown in membrane bioreactors where it was observed that a predominance of cellular nodules, indicative of cell proliferation, were formed primarily at the nutrient inlet. When the cells were cultured in the bioreactor system 10 utilizing the four way LL valve 16, nodules were apparent throughout the hollow fiber module. Additionally, the hollow fiber module was split open and individual fibers were examined microscopically with and without the aid of stain, Hematoxylin and Eosin, and uniform cell proliferation was observed at both ends of the fibers.

EXAMPLE III

A hollow fiber bioreactor system 110 was constructed as depicted in FIG. 6. The system was autoclave sterilized, except for the hollow fiber oxygenator 60, which was aseptically inserted in the return nutrient line as depicted. The system was then filled with a culture medium, modified Frey's medium supplemented with 8% porcine serum, pH 7.0, through the sterile barrier tangential flow device 2, and incubated for 48 hours at 37° C. in ambient air as a check for sterility and system equilibration.

A 20 milliliter 0.1% cell suspension of Mycoplasma galasepticum was inoculated into the extracapillary space (interstitial passages) of the hollow fiber bioreactor 112. The system was then incubated for 35 days with media being changed as required based on the cell densities extracted from the extracapillary space. The four way LL valve 216 was automatically switched every minute by a timing device 34 produced by Eutectic Electronic, Raleigh, N.C.

Mycoplasma species are routinely grown in suspension cultures at densities of 0.4% cells or less, and have an affinity for fiber membranes and plastics. Therefore, the hollow fiber bioreactor 212 utilized in this experiment, as supplied by Applied Membrane Technologies, Minnetonka, Minn., had two major modifications: 1) a polyolefin coating was placed on the 0.1 micron base membrane to counteract the Mycoplasma's tendency to adhere to the membrane fibers, 2) the extracapillary space had four exit ports. Two of the diagonally opposed ports were connected by tubing through a Cole-Parmer peristaltic pump 263 as shown in FIG. 6. The pump was utilized to assure complete uniformity of the culture by preventing adherence of the organisms to the fibers and to give added mixing to the extracapillary space nutrients.

The extracapillary space pump 263 was evaluated in two different operational modes: (1) a continuous slow recirculation of the nutrient medium; and an (2) intermittent mode of 1 minute on and 5 minutes off. The second method was hypothesized to be less disruptive to general protein stability. The recirculation rate for pump 263 was set at one system volume per minute.

The Mycoplasma cells were the desired product of these experiments. Special emphasis was place don being able to harvest a uniformly dispersed cell suspension with the highest possible cell densities.

Several preliminary experiments were performed using this organism, with notable results. In the first experiment, without a four way LL valve 216 or extracapillary pump 263, a cell suspension of roughly 1 to 2% was observed growing and adhering to the fibers at the inlet port of the bioreactor 12. A second experiment, where the four way LL valve 216 was utilized, but not the extracapillary pump 263, cell densities of 4.0% were achieved. The organisms were evenly dispersed the length of the bioreactor 212, but continued a close proximity to the fibers. This adhesion of the organisms to the fibers made harvesting a uniform suspension difficult. In the last experiment, utilizing the four way valve and external flow circuit components as shown in FIG. 6, yields of uniformly dispersed 10% cell suspensions were routinely harvested at twelve hour intervals.

In the foregoing experiments, a hollow fiber oxygenator 60, commercially available from CD Medical Corp., Miami Fla., was employed, along with a Biostat M fermentor (B. Braun, West Germany) as the nutrient medium reservoir 230. The oxygenator 60 was employed to facilitate oxygenation of the nutrient medium rather than sparging through the medium in reservoir 230. No remarkable change in growth was expected or observed due to the oxygenator 60, which was added merely for convenience and evaluation purposes. The B. Braun fermentor was employed to overcome a shortage of available warm room space for temperature control, and to provide automatic rather then manual pH monitoring and control, as a test of the overall system integrity when operated in a manufacturing mode. The increased cell growth observed was not attributable to the automatic pH control insofar as the pH monitor and control were shut off for several days to directly test that hypothesis.

A sterile barrier tangential flow device 2, commercially available from Microgon Inc., Laguna Hills, Calif., was used in the second and succeeding experiments for all media exchanges. The enhanced security afforded by this sterile barrier tangential flow device was highly beneficial. The last Mycoplasma experiment was performed using the aforementioned fermentor, without the benefit of a sterile hood or other containment apparatus. There were more than seventy nutrient media exchanges during this experiment without loss of sterility.

An additional provision was made for sterility in all of the aforementioned experiments on Mycoplasma. This involved the use of two series-connected two way valves (Becton Dickenson) on all hollow fiber membrane cartridge ports. This dual valve arrangement allowed for resterilization of the outermost valves with alcohol on plastic valves, or flame on stainless valves, while the inner valve remained closed assure a sterile barrier. The dual-valve arrangement was indispensible for the harvesting of the cells from the extracapillary space of the bioreactor 212. The dual valves 242 and 248 made it possible to retain a sterile environment in the extracapillary space, despite over 100 samples having been drawn during the last experiment alone.

From the foregoing it can be seen that the apparatus and method of the invention provide a relatively simple bioreactor system which dramatically improves equal dispersion of cell growth throughout the growth chamber, enhances the transport of metabolic waste away from the cells, and overall produces a more homogeneous environment for other metabolic parameters. Thus, the principal objects of the invention have been achieved. Other incidental advantages include the ability to use relatively simple plumbing which is easy to assemble and maintain. Another practical advantage is the minimum number of fittings required which lowers the potential incidence of breaks in sterility. It is also recognized that the flow of nutrient medium through the growth chamber could be controlled in a more complex manner through the provision of a plurality of valves, however, the control of a single valve is inherently more desirable, and accurate, than controlling several valves. Further, valve failure of the four-way valve in the system of the invention would not of itself cause cell death.

Although specific embodiments and features of the invention has been described in detail, it will be appreciated that other variations, modifications and embodiments thereof are possible, and accordingly, all such variations, modifications, and embodiments are to be regarded as being within the spirit and the scope of the invention.

What is claimed is:

1. A mass transfer method comprising:
   (a) establishing a mass transfer system which includes:
      (i) a first pump having inlet and discharge ports;
      (ii) an elongated mass transfer chamber having first and second inlets at opposite ends of the chamber to accommodate flow of a first mass transfer medium therethrough in mass transfer relationship with a second mass transfer medium therein;
      (iii) a first mass transfer medium reservoir having inlet and outlet ports;
      (iv) switchable flow control means comprising flow ports designated A, B, C, and D, for connecting:
         (1) in a first configuration, port A in flow communication with port B, and port C in flow communication step D; and
         (2) in a second configuration, port A in flow communication with port D, and port B in flow communication with port C;
      (v) conduits connecting the pump discharge port to said port C, the pump inlet port to the reservoir outlet port, the reservoir inlet port to said port A, the chamber first inlet to said port B and the chamber second inlet to said port D;
   (b) operating said first pump to establish flow of said first medium through said mass transfer chamber in a selected direction; and
   (c) periodically repositioning said switchable flow control means so as to sequentially change according to a predetermined schedule the direction of flow of said first medium through said mass transfer chamber.

2. A method according to claim 1, wherein at least one mass transfer surface element is provided in said chamber defining passages on its respective sides, the passage(s) on one side of said element(s) communicating with said first and second inlets for flow of said first medium therethrough in mass transfer relationship with said second medium in the passage(s) on the other side of said element(s).

3. A method according to claim 2, comprising flowing said second medium through said passage(s) on the other side of said element(s).

4. A method according to claim 2, wherein said second medium from said mass transfer chamber is periodically circulated through an external flow circuit communicating with said passage(s) on the other side of said element(s).

5. A method according to claim 1, wherein said second medium is selected from the group consisting of cell cultures, blood, and pharmaceutical compositions.

6. A method according to claim 2, wherein said mass transfer chamber is provided with a port communicating with said passage(s) on the other side of said element(s), with two serially-connected valves connected to said port, including a first valve contiguous to said port and a second valve contiguous to said first valve, comprising sterilizing said second valve in an opened position while said first valve is closed.

7. A method according to claim 1, comprising providing a supply reservoir of said second medium and pumping said second medium from said second medium supply reservoir through said chamber and back to said second medium supply reservoir.

8. A method according to claim 1, wherein said second medium is a cell culture and said first medium is a nutrient medium therefor.

9. A method according to claim 8, wherein said first medium flowed through the conduit connecting the reservoir inlet to port A is oxygenated upstream of said reservoir.

10. A method according to claim 1, comprising:
    (d) periodically pumping said second medium from said mass transfer chamber through an external flow circuit;
    (e) agitating the first medium in said reservoir; and
    (f) remotely controlling:
       pumping rate in steps (h) and (d);
       periodicity of pumping step (d);
       valve positioning in step (c); and
       agitation rate in step (e).

11. A method according to claim 10, wherein said remote controlling steps are carried out at a unitary remote locus.

12. A method according to claim 1, wherein said switchable flow control means is a four way valve.

13. A cell growth method comprising:
    (a) establishing a sterile growth system which includes:
       (i) a pump having discharge and inlet ports;
       (ii) an elongated cell growth chamber having first and second inlets at opposite ends of the chamber;
       (iii) a nutrient medium reservoir having inlet and outlet ports;
       (iv) switchable flow control means comprising flow ports designated A, B, C, and D, for connecting:
          (1) in a first configuration, port A in flow communication with port B, and port C in flow communication with step D; and
          (2) in a second configuration, port A in flow communication with port D, and port B in flow communication with port C;
       (v) conduits connecting the pump discharge port to said port C, the pump inlet port to the reservoir outlet port, the reservoir inlet port to said port A, the chamber first inlet to said port B and the chamber second inlet to said port D;
    (b) introducing culture medium to the system;
    (c) inoculating the chamber with a selected cell type;
    (d) operating said pump to establish flow of said medium through said growth chamber in a selected direction;
    (e) incubating the system for a selected period and during such period changing the medium if and as required for the selected medium; and
    (f) periodically repositioning said switchable flow control means so as to sequentially change according to a predetermined schedule the direction of flow through said growth chamber, to substantially uniformly disperse cell growth throughout said chamber and transport metabolic waste away from the cells being grown in said chamber.

* * * * *

UNITED STATES PATENT AND TRADEMARK OFFICE
CERTIFICATE OF CORRECTION

PATENT NO. : 6,048,727
DATED : April 11, 2000
INVENTOR(S) : Henry B. Kopf

It is certified that error appears in the above-identified patent and that said Letters Patent is hereby corrected as shown below:

Column 1, lines 30-31: change "frequency" to -- frequent --

Column 9, line 7: change "conduit 22" to -- conduit 222 --

Column 12, line 65: change "the" to -- The --

Column 13, line 51: change "was place don" to -- was placed on --

Signed and Sealed this

Eighth Day of May, 2001

Attest:

NICHOLAS P. GODICI

Attesting Officer

Acting Director of the United States Patent and Trademark Office